US012336811B2

(12) United States Patent
Gericke Estermann et al.

(10) Patent No.: US 12,336,811 B2
(45) Date of Patent: Jun. 24, 2025

(54) MEASURING DEVICE FOR DETERMINING THE BLOOD SUGAR CONTENT

(71) Applicants: Monika Gericke Estermann, Zürich (CH); Ivan Ivanowitsch Turkovski, Zollikon (CH)

(72) Inventors: Monika Gericke Estermann, Zürich (CH); Ivan Ivanowitsch Turkovski, Zollikon (CH)

( * ) Notice: Subject to any disclaimer, the term of this patent is extended or adjusted under 35 U.S.C. 154(b) by 959 days.

(21) Appl. No.: 17/430,418

(22) PCT Filed: Feb. 13, 2020

(86) PCT No.: PCT/EP2020/053760
§ 371 (c)(1),
(2) Date: Aug. 12, 2021

(87) PCT Pub. No.: WO2020/165344
PCT Pub. Date: Aug. 20, 2020

(65) Prior Publication Data
US 2022/0151520 A1 May 19, 2022

(30) Foreign Application Priority Data
Feb. 13, 2019 (DE) .................... 10 2019 103 641.0

(51) Int. Cl.
A61B 5/145 (2006.01)
A61B 5/00 (2006.01)
(Continued)

(52) U.S. Cl.
CPC .......... *A61B 5/14532* (2013.01); *A61B 5/053* (2013.01); *A61B 5/263* (2021.01); *A61B 5/681* (2013.01); *A61B 2562/066* (2013.01)

(58) Field of Classification Search
CPC ..... A61B 5/14532; A61B 5/263; A61B 5/053; A61B 5/681; A61B 2562/066
(Continued)

(56) References Cited

U.S. PATENT DOCUMENTS 6,408,200 B1 6/2002 Takashina
7,215,989 B1 5/2007 Burks
(Continued)

FOREIGN PATENT DOCUMENTS

DE 102005039038 A1 2/2007
EP 2344025 B1 11/2013

OTHER PUBLICATIONS

Examination Report created Jun. 15, 2020 in related/corresponding DE Application No. 10 2019 103 641.0.
(Continued)

Primary Examiner — Alex M Valvis
Assistant Examiner — Chanel J Jhin
(74) Attorney, Agent, or Firm — PATENT PORTFOLIO BUILDERS PLLC

(57) ABSTRACT

A measuring device determines an estimated value for a person's blood sugar content using a non-invasive impedance measurement. The measuring device includes a measurement transducer for determining a blood sugar content from a measured value and a sensor unit for detecting the measured value. The sensor unit has at least two tetrapolar electrode assemblies, each having at least two electrode pairs arranged along a first linear axis. Axes of the two tetrapolar electrode assemblies are aligned perpendicularly to one another. A first electrode pair transmits and receives a current signal, and a second electrode pair taps a potential on contact with the skin of the person. At least one of the electrodes of the sensor unit has a contact surface for contacting the skin, which contact surface consists of a metal
(Continued)

or a metal alloy having a conductivity of more than $1*10^7$ S/m.

15 Claims, 9 Drawing Sheets

(51) Int. Cl.
*A61B 5/053* (2021.01)
*A61B 5/263* (2021.01)

(58) Field of Classification Search
USPC .......................................................... 600/365
See application file for complete search history.

(56) References Cited

U.S. PATENT DOCUMENTS

| | | | |
|---|---|---|---|
| 2009/0033333 A1 | 2/2009 | Gribova et al. | |
| 2012/0209101 A1 | 8/2012 | Kidmose et al. | |
| 2015/0366493 A1* | 12/2015 | Cremers | A61B 5/4362 205/264 |
| 2019/0000357 A1* | 1/2019 | Ross | A61B 5/0531 |
| 2020/0003592 A1* | 1/2020 | Sulzer | G01F 1/584 |

OTHER PUBLICATIONS

International Search Report mailed May 13, 2020 in related/corresponding International Application No. PCT/EP2020/053760.
Käszmann et al.; "Edelmetalle für Technische Ober Flächen—Ein Blick Auf Die Eigenschaften;" WOTech Technical Media; Oct. 10, 2013; https://www.wotech-technical-media.de/womag/ausgabe/2013/10/21_w_edelmetalle_schade_10j2013/21_w_edelmetalle_schade_10j2013.php.
Kusche et al.; "Dry electrodes for bioimpedance measurements—design, characterization and comparison;" IOP Biomedical Physics & Engineering Express; Oct. 2018; vol. 5, No. 1.
Wikipedia; "Elektrische Leitfähigkeit;" Dec. 17, 2018; https://de.wikipedia.org/w/index.php?title=Elektrische_Leitf%c3%A4higkeit&oldid=183798162.
Wikipedia; "Galvanotechnik;" Jun. 20, 2018; https://de.wikipedia.org/w/index.php?title=Galvanotechnik&oldid=178476732.
Written Opinion mailed May 13, 2020 in related/corresponding International Application No. PCT/EP2020/053760.

* cited by examiner

Fig. 5a
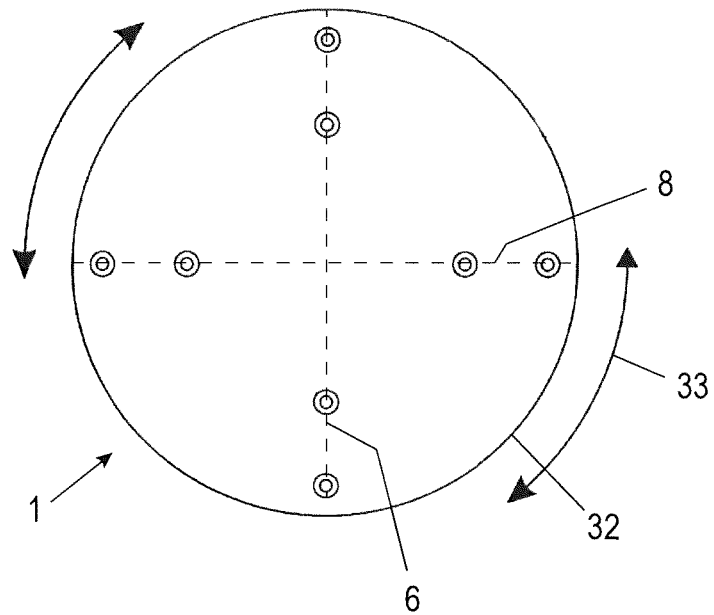
Fig. 5b
Fig. 5c
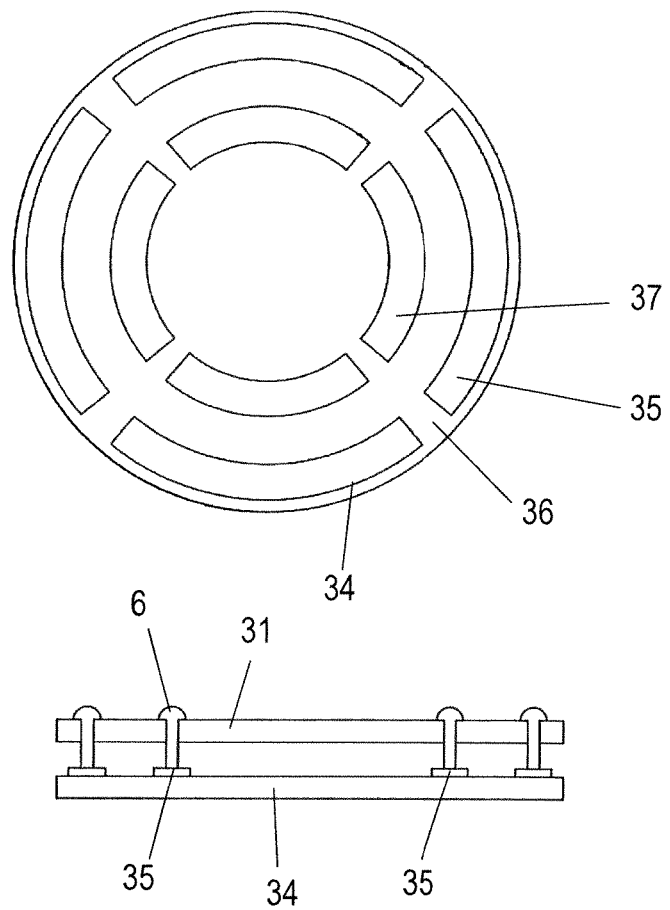

MEASURING DEVICE FOR DETERMINING THE BLOOD SUGAR CONTENT

BACKGROUND AND SUMMARY OF THE INVENTION

Exemplary embodiments of the present invention relate relates to a measuring device for determining the blood sugar content using a non-invasive impedance measurement.

EP 2 344 025 A1 discloses a device for determining the blood sugar content or for evaluating a glucose change in the blood of a human.

The use of bar-shaped electrodes is known from EP 2 344 025 A1. Electrodes for the aforementioned field of application are typically made of a resistant metal that exhibits high wear resistance and also high chemical inertness against oxidation. Stainless steel electrodes, for example, are therefore suitable.

However, the sensor unit of EP 2 344 025 A1 requires a comparatively large amount of space due to the design of the electrodes. The size of the contact area should not be too small to ensure that the measured values are recorded, taking into account the conductivity of the stainless steel electrodes.

Based on the aforementioned problem, exemplary embodiments of the present invention are directed to an optimal acquisition of the impedance data.

A measuring device according to the invention is used to determine an estimated value for the blood sugar content of a person by means of a non-invasive impedance measurement. The impedance measurement enables a statement to be made about the change in volume of the interstitial fluid compartments and thus the osmotic pressure. This in turn changes according to the blood glucose level. In particular, the measuring device measures the sugar content in the interstitial tissue.

To evaluate the impedance measurement, the measuring device has a measurement transducer that can determine a change in blood sugar content from a reading of the impedance measurement.

Furthermore, the measuring device has a measuring sensor in the form of a sensor unit for recording at least one measured value, in particular several different measured values. The measurement can take place discontinuously at intervals or continuously. The measuring device can preferably be battery-operated.

The sensor unit comprises at least two tetrapolar electrode assemblies, which each have at least two pairs of electrodes, i.e., four electrodes, which are arranged along a first linear axis.

The axes of the two tetrapolar electrode assemblies are aligned perpendicularly to each other. A first pair of electrodes is used to transmit and receive a current signal and a second pair of electrodes is used to tap a potential while in contact with the skin of the person.

At least one of the electrodes of the sensor unit, in particular all electrodes of the tetrapolar electrode assemblies, have a contact surface for contacting the skin, which contact surface consists of a metal or a metal alloy with a conductivity of more than $1*10^7$ S/m. The conductivity relates to a measurement under standard conditions, i.e., at a temperature of 20° C. and normal pressure.

By selecting the electrode material with the aforementioned high conductivity, reliable signal reception can be ensured and at the same time the contact area of the electrodes can be reduced to a minimum. As a result, many electrodes can be arranged in the area of the sensor unit without causing a short circuit between the electrodes.

Preferably, the metal of the contact surface may be formed of gold, rhodium, tantalum, iridium, tungsten, and/or osmium. Alternatively, at least 40% by weight of the metal alloy may be formed from one or more of the aforementioned metals.

The electrode can have an inner electrode made of a noble metal, in particular gold, and a support sleeve made of a material with a Vickers hardness of more than 40, according to DIN EN 6507-1:2018-07. The support sleeve protects the inner electrode from mechanical wear. The support sleeve can also be made of a silicon compound with a thermal conductivity of more than 100 W/(m*K). Particularly preferably, the material of the support sleeve in this case also corresponds to a Vickers hardness of more than 40. All thermal conductivities in the present invention refer to a measurement at 0° C. and a humidity of 50%.

The electrode can have an electrode body made of copper and/or brass and/or a silicon compound, in particular alpha-silicon carbide, wherein the body is provided with a coating of rhodium, tantalum, iridium and/or osmium to form the contact surface. As a result, the electrode surface has a chemically inert contact surface. With this variant of the electrode, the support sleeve can be omitted.

A combination of copper or bronze as the inner electrode and rhodium as the coating is particularly preferred.

The aforementioned coating can have a coating thickness of at least 2 μm, preferably between 3 to 10 μm, over the entire contact area.

The sensor unit can have a plate or a leather segment on which the tetrapolar electrode assemblies are fixed, in particular anchored, wherein the plate or the leather segment for integration in a flexible wristband has a fatigue bending strength according to DIN EN ISO 5402-1:2017-05 or ISO 4666-2 of 100,000 folds without damage. This can be verified by measurement with a flexometer.

One electrode in each case can be arranged in an opening in the plate and/or the leather strip, with the support sleeve having a radial projection as a stop on the surface of the plate or the leather strip at the edge of the opening. This enables the electrode to be positioned securely on or in the plate or in the leather strip. For example, a plastic, e.g., a rubber, or Alcantara can also be used as the material of the plate.

The maximum extension of the contact surface is referred to below as the width. This width, in the case of a round electrode this corresponds to the diameter, of the contact surface of the electrode, in particular of the inner electrode, can be less than 5 mm, preferably 2-3 mm.

The electrode or at least the inner electrode can be designed as a round electrode, in particular as a mushroom-head electrode. A round electrode with a contact surface that is symmetrical in all directions enables a more precise determination of impedance anisotropies.

The sensor unit can preferably have four or eight tetrapolar electrode assemblies, each with two pairs of electrodes arranged on a linear axis.

The electrodes of the sensor unit may be arranged on two circular paths, preferably arranged concentric to each other, wherein the number of electrodes on the first circular path is equal to the number of electrodes on the second circular path.

The diameter of the first circular path can be between 20 to 40 mm and the diameter of the second circular path can be at least 30% smaller than the diameter of the first circular path.

The distance between two adjacent electrodes of two adjacent electrode assemblies can be more than 4 mm, preferably between 5 and 8 mm, to avoid signal transmission.

The arrangement of the electrodes of the sensor unit can be point-symmetrical and in particular mirror-symmetrical.

Preferably, the measuring device is designed as a portable measuring device with a wrist strap and/or foot strap t, wherein the sensor unit has a width parallel to the wrist strap and/or foot strap width of less than 40 mm, preferably between 15-35 mm.

The sensor unit can have an element, preferably plate-shaped, which can be rigidly connected to the person, wherein the electrodes of the electrode assemblies, in particular the axes of the electrode assemblies, are arranged rotatably about an axis of rotation relative to the plate-shaped element.

The plate-shaped element can be, for example, a printed circuit board. A base plate or a ring plate or a combination of both is recommended for fixing the electrodes with constant electrode spacing on a circular path.

The aforementioned element can advantageously have circular arc-shaped contact surfaces for signal pickup from the electrodes.

For the purpose of virtual rotation, the axis of one of the tetrapolar electrode assemblies can be arranged at an angle to a second axis of a further electrode assembly, starting from a common electrode as an angular vertex, wherein the signal tapping is controlled by a control unit in such a way that, for the purpose of virtual rotation of the electrode assembly, the signals are tapped selectively at the electrodes of the first or the second axis.

BRIEF DESCRIPTION OF THE DRAWING FIGURES

Further advantages, features and details of the invention will be apparent from the following description, in which several exemplary embodiments of the invention are explained in more detail with reference to the accompanying drawings. The person skilled in the art will conveniently also consider the features disclosed in combination in the drawings, the description and the claims individually and combine them to form useful further combinations, wherein:

Figure 6A:
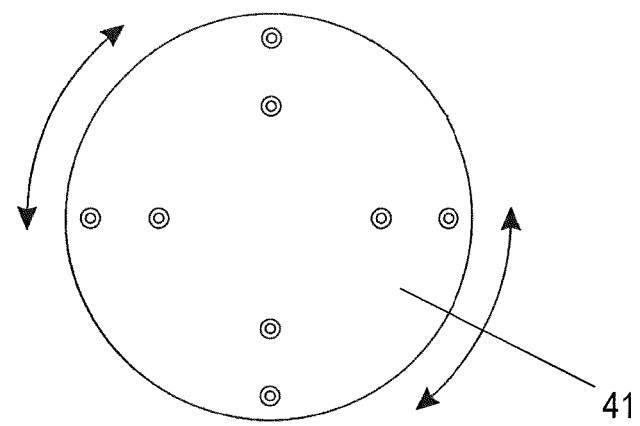
Figure 7A:
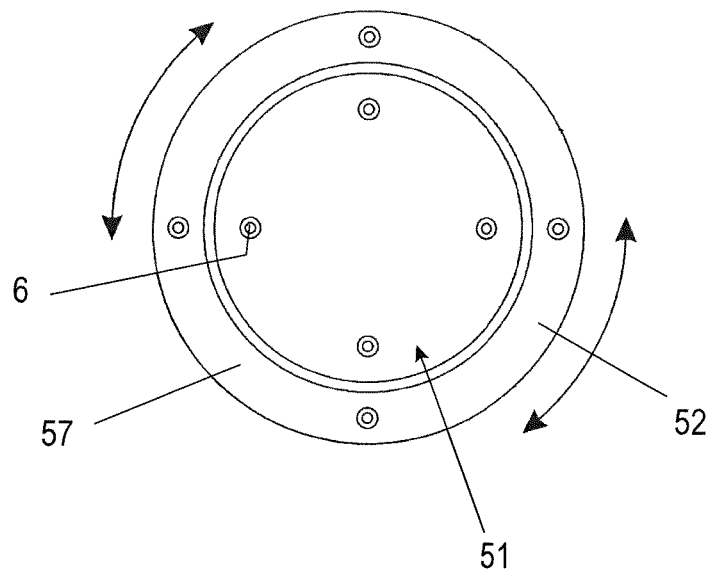
Figure 8:
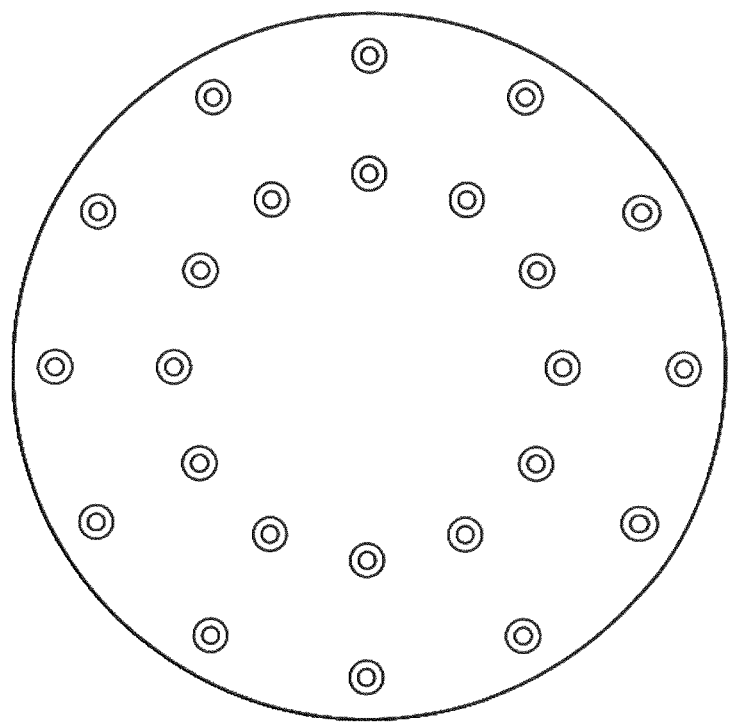
Figure 9:
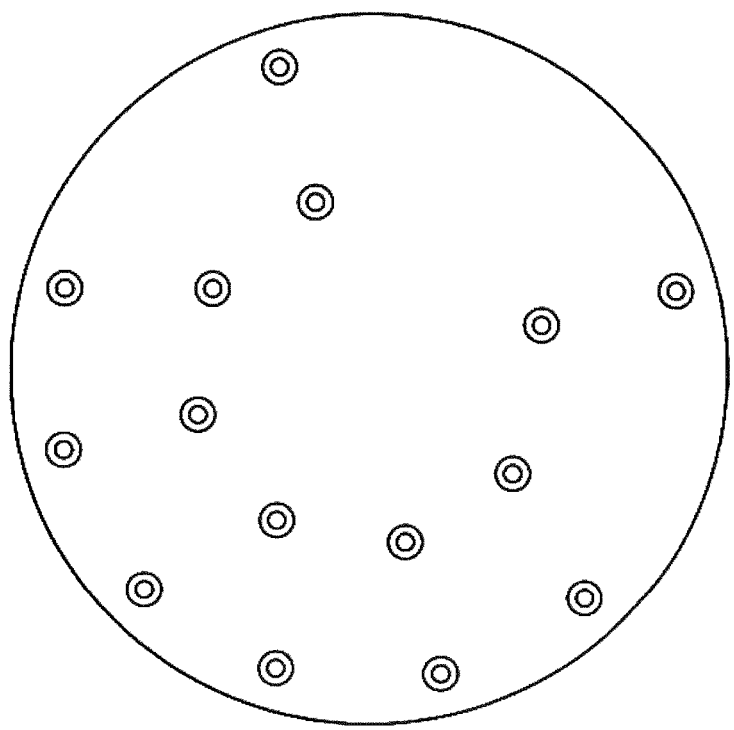
Figure 10A:
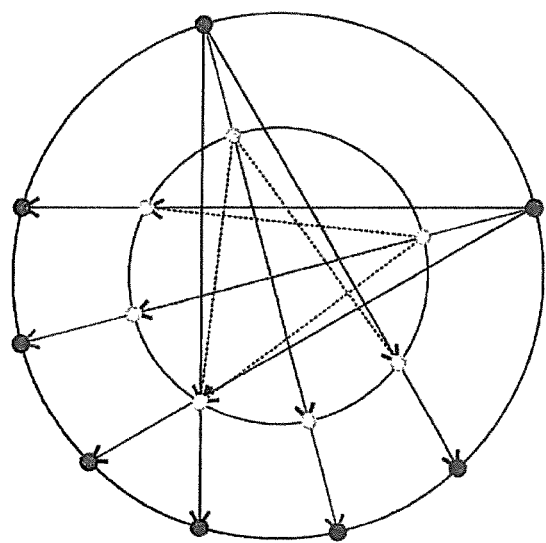
Figure 10B:
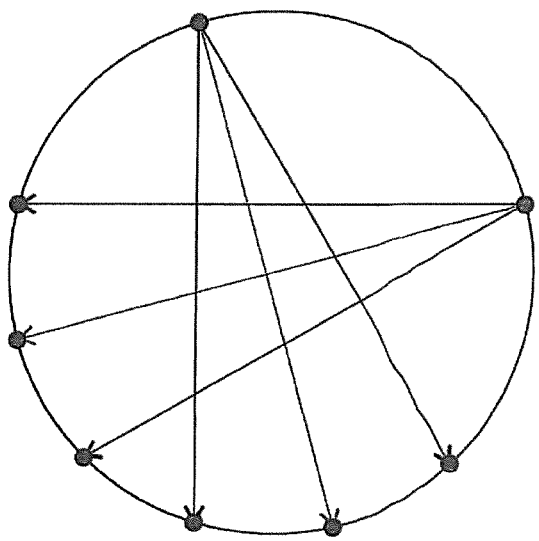

FIGS. 5a)-c) show a top view of a second variant of a sensor unit for skin contact;

FIGS. 6a)-c) show a top view of a third variant of a sensor unit for skin contact;

FIGS. 7a)-c) show a top view of a fourth variant of a sensor unit for skin contact;

FIG. 8 shows a top view of a fifth variant of a sensor unit for skin contact;

FIG. 9 shows a top view of a sixth variant of a sensor unit for skin contact;

FIGS. 10a)-b) show a top view of measuring and compensation axes for the sensor units of FIGS. 8 and 9.

DETAILED DESCRIPTION

Figure 1:
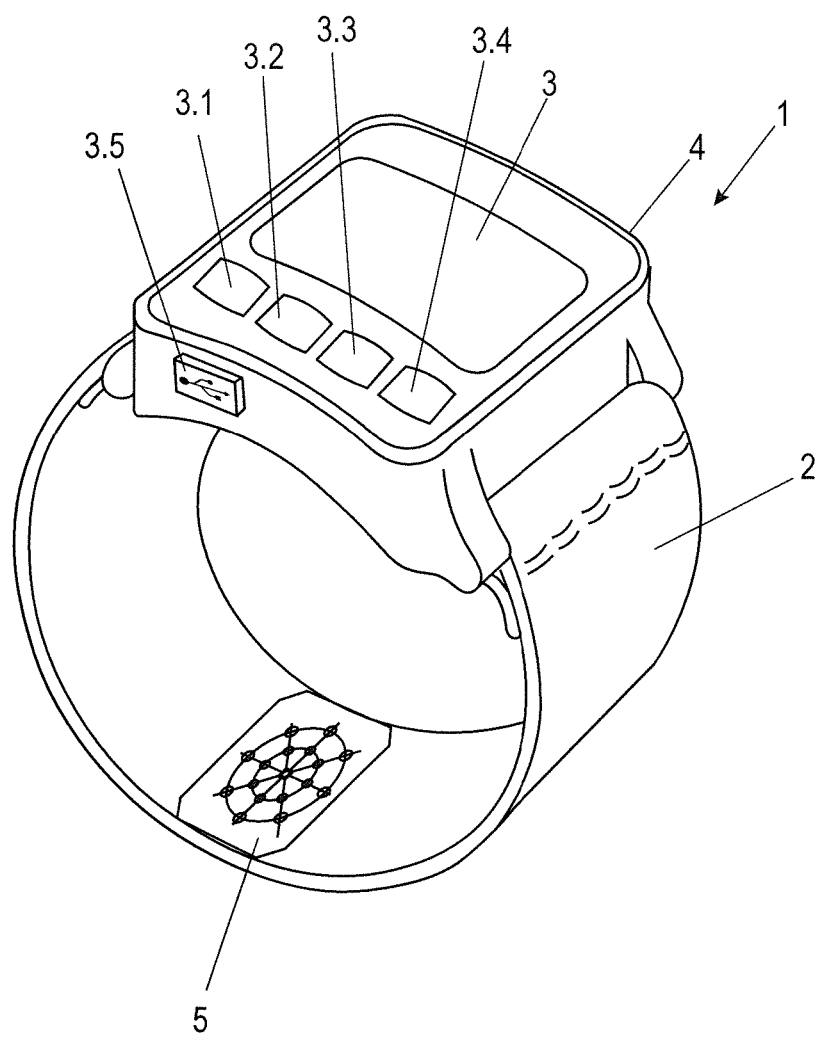
FIG. 1 shows a schematic representation of a glucose measuring device.

FIG. 1 shows a schematic representation of a measuring device 1 for determining a change in blood sugar content. This measuring device can even determine the blood sugar content as an absolute value if the initial content is known. A typical embodiment of the measuring device according to the invention is a glucose measuring device 1 whose mode of operation is already described, inter alia, in EP 2 344 025 A1. This device is used to carry out a non-invasive method for estimating the glucose level in the blood of a person.

This glucose level can be determined by measuring the impedance, with a measurement of the impedance of the skin occurring first. For this purpose, an arrangement of at least two electrodes, a transmitting and a receiving electrode, is assumed. An electric current is transmitted between the electrodes via the skin and at the same time a potential difference is determined, which results due to the skin in the space between the electrodes. The currents and potentials determined can be used to determine an estimated value for a glucose value, analogous to EP 2 344 025 A1.

The glucose measuring device 1 comprises a wrist strap 2 for fixing the glucose measuring device to an arm, in particular a wrist. Alternatively, it is also possible to attach it to an ankle or foot or to another part of the body. In these areas, there is also a very large anisotropy of the body's own impedance.

The wristband can be made of metal, leather, or a textile material, analogous to the wristband of a wristwatch, wherein a signal conductor, e.g., a flexprint conductor plate, is preferably incorporated into the wristband.

The glucose measuring device 1 comprises a measurement transducer 4 with evaluation electronics for evaluating impedance measurement data and for determining information regarding a glucose level determined from the measurement data. Furthermore, the measurement transducer 4 comprises a display 3 for outputting the aforementioned information.

Below the display 3, several operating elements 3.1-3.4, e.g., keys, are arranged, with which several display options can be selected. Furthermore, setpoints or other menu elements can be set via the operating elements.

A further edge-side operating element 3.5 enables activation of a radio connection, preferably via Bluetooth, for data transmission, e.g., to a computer. In this way, for example, analysis values of a previously sampled interstitial fluid compartment, e.g., the conductivity and/or the composition, can be transmitted for calibration of the glucose measuring device to improve the accuracy of the determined estimated value. However, the glucose measuring device does not necessarily require these values to determine an estimated value; instead, it starts from a basic setting with preset target values.

Figure 2:
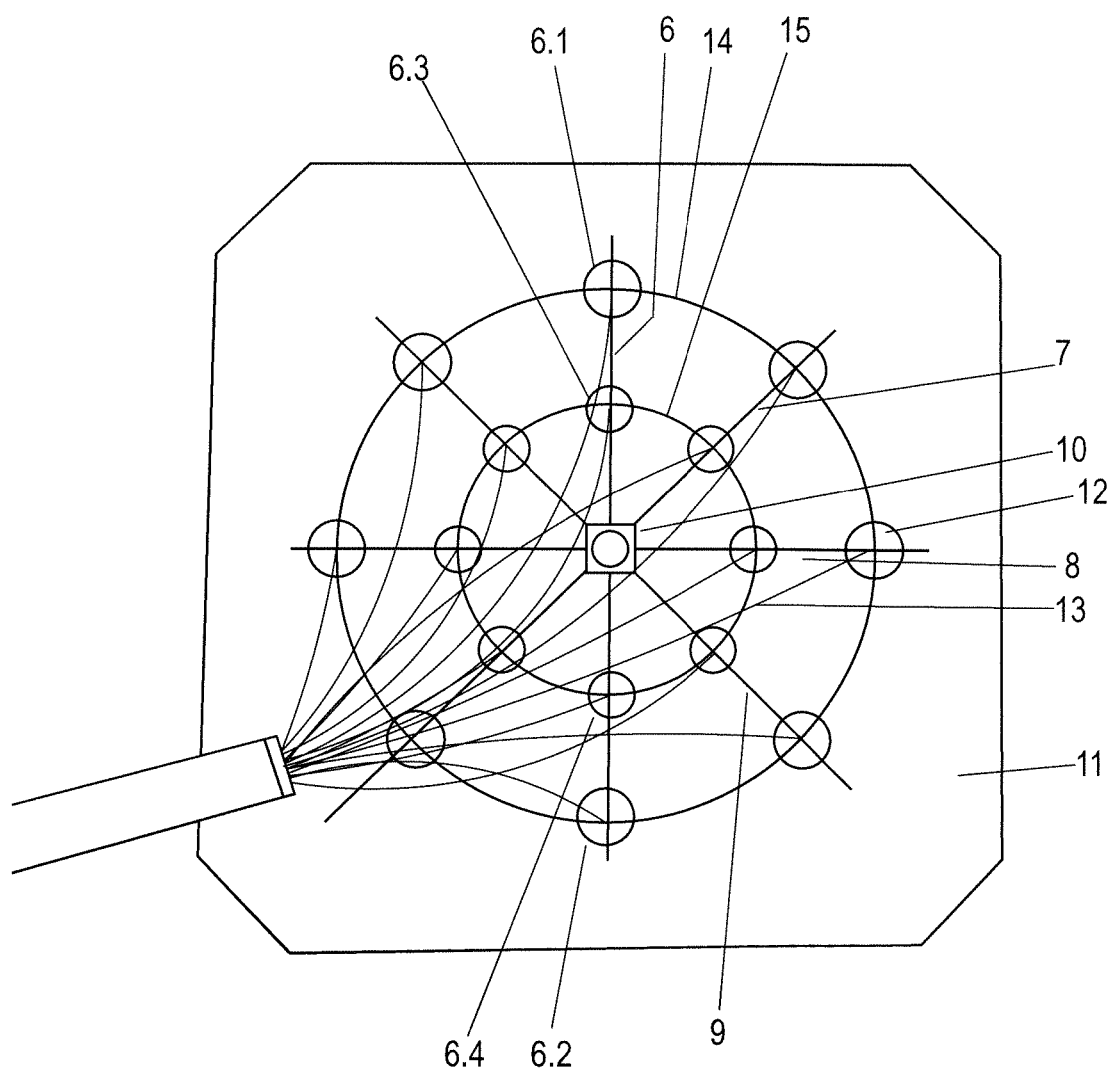
FIG. 2 shows a representation of a first variant of an electrode assembly for skin contact.

FIG. 2 shows a sensor unit 5 which can be arranged on the wristband 2 of FIG. 1, wherein the sensor unit 5 comprises an assembly of several electrodes 6.

The sensor unit 5 comprises four so-called tetrapolar electrode assemblies 6, 7, 8, and 9, each with two pairs of electrodes, which are arranged in a mirror-symmetrical arrangement with respect to each other. The skin area to be detected is enclosed between the electrodes of the electrode assemblies 6-9 of the sensor unit 5. In each case, one electrode assembly 6.1-6.4 lies on a mirror symmetry axis A and has two electrode pairs 6.1 and 6.2 or 6.3 and 6.4, between which interference occurs.

The first pair of electrodes includes electrodes 6.1 and 6.2 for transmitting and receiving a current signal.

A second pair of electrodes, comprising electrodes 6.3 and 6.4, is used to tap a potential on contact with the skin.

The respective mirror symmetry axes A-D of the tetrapolar electrode assemblies 6-9 are arranged point-symmetrically around a center point 10 of the sensor unit 5 with an offset of 45°. Optionally, a temperature sensor can be arranged in the area of the center point.

The electrodes of electrode assemblies 6-9 are arranged on a dielectric plate 11, which has a lower conductivity than the skin, so that the current signal is transmitted through the skin rather than through a short circuit between the electrodes.

Decisive factors for the measurement accuracy of the sensor unit 5 include, among others, the number of electrode assemblies, the dimension of a contact surface 12 of the respective electrode with the skin and its distance from an adjacent electrode.

The electrodes of the electrode assembly 6-9 each have an electrical line 13 on the side opposite their contact surface 12 for supplying power to the electrodes and for tapping the received measurement signals.

The distance between an electrode 6.1 or 6.2 of the first electrode pair of a first electrode assembly 6 and an electrode of a first electrode pair of an adjacent second electrode assembly 7 is more than 8 mm, preferably between 10 and 15 mm, starting from the center point of a contact surface 12 of one electrode to the center point of the contact surface 12' of the adjacent electrode. It is understood that the aforementioned sizes are only preferred and the distances can also be larger or smaller.

The distance between an electrode 6.3 or 6.4 of the second electrode pair of a first electrode assembly 6 and an electrode of a second electrode pair of an adjacent second electrode assembly 7 is more than 4 mm, preferably between 5 and 8 mm, starting from the center point of a contact surface 12 of one electrode to the center point of the contact surface 12' of the adjacent electrode. It is understood that the aforementioned sizes are only preferred and the distances can also be larger or smaller.

The electrodes of the first electrode pair 6.1 and 6.2 are arranged diametrically opposite each other on a first circular path 13 and the electrodes 6 of the second electrode pair 6.3 and 6.4 are arranged diametrically opposite each other on a second circular path 14.

The two circular paths are aligned concentrically to each other, wherein the diameter of the first circular path is between 20 to 40 mm, and wherein the diameter of the second circular path 14 is at least 30% smaller than the diameter of the first circular path 13. It is understood that the aforementioned diameters are only preferred and can also be larger or smaller.

On each circular path 13 and 14, eight electrodes are arranged at equidistant distances from each other.

The minimum number of electrodes per circular path is 8. In this case, there are only two tetrapolar electrode assemblies, each with four electrodes on a symmetry axis, wherein the symmetry axes are arranged perpendicularly to each other However, the measurement accuracy is increased with the number of electrode assemblies. For space reasons, however, a number of electrodes greater than 32 is not recommended.

In the following, the structure of a single electrode 20 of the electrode assemblies 6-9 is explained in more detail with reference to FIG. 3. The electrode 20 shown can, for example, be one of the electrodes 6.1-6.4. Preferably, all electrodes shown in FIG. 2 can be of identical design. They have an inner electrode 21 made of a material with high conductivity.

It is desirable for an electrode 20 to have as small a contact area as possible in order to arrange as many electrode assemblies 6-8 as possible in a point-symmetrical manner next to each other on the plate 11. The electrode area depends, among other things, on the electric current density, which is limited to 1 A/m$^2$ for physiological reasons. In the case of the electrode 20 shown in FIG. 3, which is optimized in size for the intended use, an inner electrode 21 can be made of silver, rhodium, iridium, osmium, tantalum, copper, gold, and/or aluminum or corresponding metallic alloys, such as brass, with a content of one or more of the aforementioned metals of at least 40% by weight.

Optimally, the electrical conductivity of the material of the inner electrode 21 of the electrode 20 should be at least $1*10^7$ S/m.

Particularly preferred as the material of the inner electrode 21 or at least for the contact surface 12 is gold, especially gold with at least 10 carats, preferably at least 20 carats and especially preferably with at least 24 carats. This metal is chemically inert, in particular in contrast to copper and silver, which have a tendency to oxidize, and is thus suitable for skin contact.

Rhodium, iridium, osmium, or tantalum can also be used as solid electrodes and/or coatings. These metals can be applied as a coating to a copper or brass electrode, providing the chemically inert contact surface 12, forming an inert contact surface. Thus, an inner electrode 21 having a copper body and a terminal gold, rhodium, iridium, tantalum, and/or osmium coating, forming the contact area 12, is a suitable option.

The inner electrode 21 has the form of a so-called mushroom-head electrode, i.e., an electrode shaft 22 and a cap-shaped projection 23 projecting terminally in the radial direction from the electrode shaft 22, which forms a curved contact surface 24. The projection 23 has a preferred diameter of less than 5 mm, preferably 2-3 mm, in the radial direction, perpendicular to the longitudinal axis A of the electrode.

A signal line 25 is arranged at an opposite end of the inner electrode 21, for supplying power to the inner electrode 21 and/or for a signal tap from the inner electrode 21.

The signal line 25 may be connected to the inner electrode 21 via a solder connection 26.

Since gold, but also the other aforementioned materials, have only a low wear resistance, the inner electrode 21 is enclosed by a support sleeve 27 made of a material which is much more wear-resistant than the material of the inner electrode 21. Preferably, the support sleeve may be formed of titanium or steel, preferably stainless steel, or an alloy of the aforementioned metals. Alternatively, the support sleeve 27 may be formed of a ceramic or plastic material. In particular, silicon carbide is a suitable material for the support sleeve due to its optimum thermal conductivity and its great hardness. A beryllium-containing ceramic can also be considered as a material for the support sleeve. The silicon carbide as well as the beryllium-containing ceramic can also be used in combination with other materials, e.g., metals. Thus, it is conceivable that the support sleeves have the cylindrical silicon-containing or beryllium-containing sections on the inside and a cylindrical metallic section, e.g., made of stainless steel, radially outward. This cylindrical metallic section can stabilize the non-metallic material inside, for example in case of cracks in the ceramic material, towards the outside. The support sleeve 27 has an inner channel 28 parallel to the longitudinal axis A of the electrode 20, wherein the inner electrode 21 closes this channel 28 at least on one side.

It comprises a radial projection 28 in the area of the contact surface 12 of the inner electrode, which rests on the plate 11 and which serves as a support surface for the cap-shaped projection 23. In FIG. 3, the support sleeve also has a groove or a regionally or circumferentially formed undercut which serves to anchor the inner electrode in the longitudinal direction.

The plate 11 in which the electrodes are arranged can preferably be a chemically inert and electrically insulating plastic plate or a leather plate. This should have a certain flexibility. Suitable materials are, for example, leather and/or silicone. The choice of material for the plate 11 can depend on the climatic conditions in the particular area of use, such as humidity, temperature, occurrence of sandstorms, and the like.

The measurement should not only detect the surface layers of the skin, but also impedance anisotropies in underlying muscle tissue. Therefore, it is advantageous if the inner electrode 21 protrudes terminally by at least 0.5 mm, preferably at least 0.8 mm, relative to the surface of the support sleeve 27.

In the case of a coated copper and/or brass electrode, the support sleeve can advantageously be omitted by applying a conductive coating of osmium, rhodium, iridium.

Figure 3:
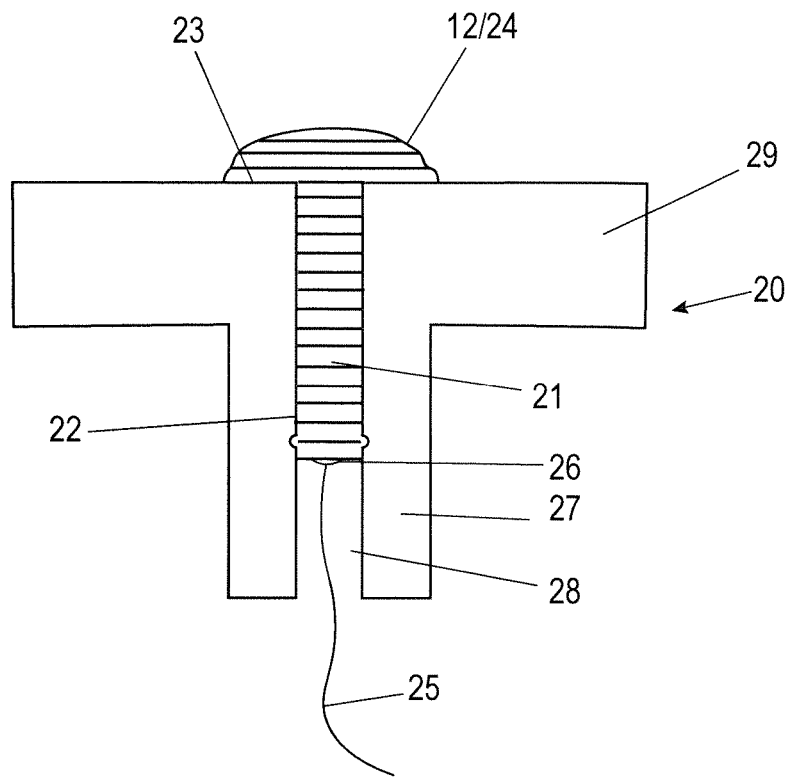
FIG. 3 shows a sectional view of an electrode.
Figure 4:
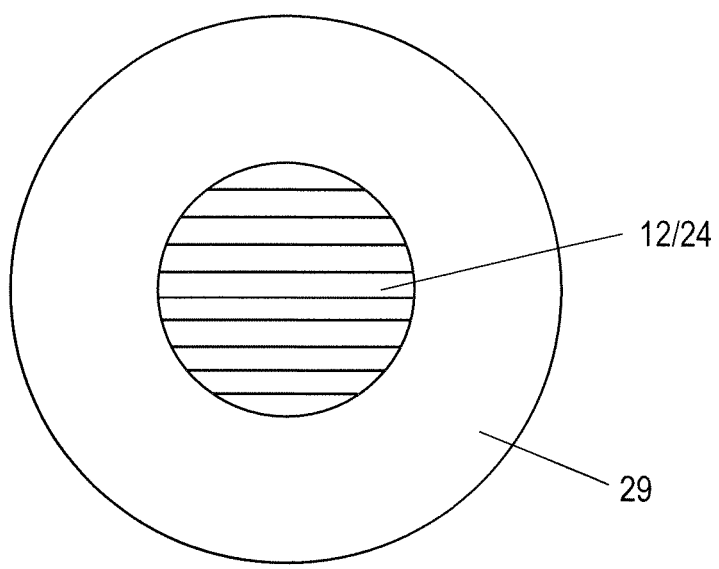
FIG. 4 shows a top view of an electrode.

FIG. 4 shows a top view of the electrode 20 of FIG. 3, where it can be seen that the diameter of the projection 28 of the support sleeve 27 is at least 50%, preferably at least 80%, larger than the diameter of the contact surface 12 of the inner electrode 21.

The electrodes shown in FIGS. 1-4 are designed as round electrodes with a round contact surface. However, it is also possible to make the electrodes strip-shaped, as shown in EP 2 344 025 A1. However, it has been shown that round electrodes are more suitable for determining impedance anisotropies in contact with the skin.

For the identification or determination of local impedance anisotropies in soft tissue below the skin by contact with the sensor, it is advantageous if the contact area of a single electrode is comparatively small. This allows a higher number of sensor axes. The small contact area of the single electrode corresponds to a high density of electric current.

The main biological effects of a high-frequency alternating current is an in-situ heating of the tissue under the electrode. Therefore, a dielectric enclosure of the electrode with a material with a high thermal conductivity is particularly advantageous.

The majority of dielectric materials are thermal insulators. However, there are some exceptions that are suitable for the application. One of them is the artificial dielectric material alpha-silicon carbide with a thermal conductivity of more than 300 W/(m*K). In addition, silicon carbide is also a very hard and chemically inert material and therefore ideal for the application described above.

Figure 7B:
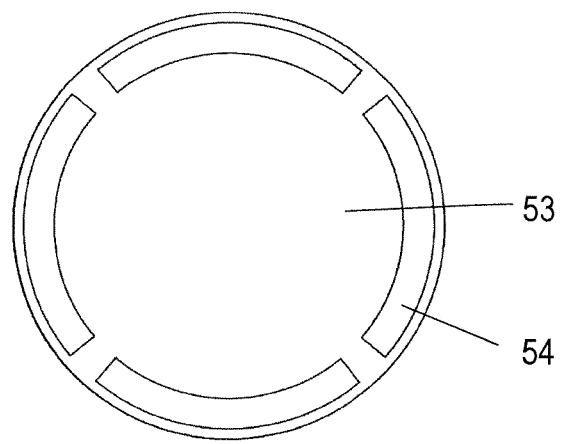
Figure 7C:
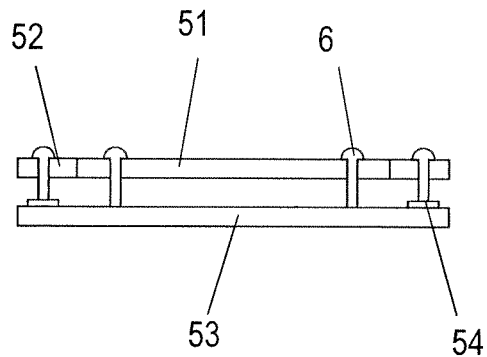

FIG. 7a-c shows individual parts of a sensor unit, which is rotatably mounted. It is well known that not all people have a uniform physiognomy. This also applies to the respective wrists. The sensor unit of FIG. 2 can be designed as a rigid arrangement with respect to the base, e.g., the wristband, which is adapted to a large number of users. Already the size of the wristband used can provide specifications regarding the wrist in this respect. In order to achieve optimum signal pickup, which may also account for anatomical peculiarities in the area of the wrist, it may be advantageous in individual cases, however, for the electrode assembly to be movable, although the distance between the electrodes should be maintained if possible.

Therefore, for patient-specific adaptation and to improve signal pickup, the electrode assembly can be mounted rotatably relative to a fixation such as a leather strap and, if necessary, also relative to an electronic board signal pickup.

FIG. 5a shows the contact side of a sensor unit with the skin in plan view with two tetrapolar electrode assemblies 6 and 8. The sensor unit has a base plate 31 and the electrodes of the electrode assemblies 6 and 8 fixed therein. The material of the electrodes and their preferred shape have been described previously.

Base plate 31 with the electrode assemblies 6 and 8 anchored therein are arranged rotatably about the center point of base plate 31 on an underlying electronics board 34, which is shown in FIG. 5b. The direction of rotation is indicated by the arrow 33. The edges 32 of the base plate 31 and the electronics board 34 are arranged flush with each other in this embodiment variant. The electronics board 34 has ring-segment-like bent contact surfaces 35 on the surface towards the base plate 31. These are used for electrical contact with the electrodes of the electrode assemblies 6 and 8 and thus for signal pickup. The curved shape of the contact surfaces 35 allows partial rotation of the base plate 31 relative to the electronics board 34 without causing contact breakage. Insulating ridges are provided between the contact surfaces 35 so that the contact surfaces are insulated from each other. The arcuate contact surfaces 35 are arranged on two circular paths 36 and 37 which are concentric with each other.

As can be seen from the sectional view in FIG. 5c, the contact surfaces for sliding contacting of the electrodes protrude from the surface of the electronics board 34. The material thickness of the contact surfaces 35 of at least 10% of the plate thickness of the electronics board 34 enables a mechanical resistance of the contact surfaces.

Figure 6B:
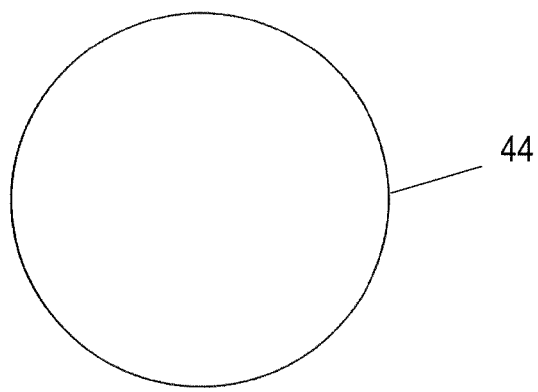
Figure 6C:
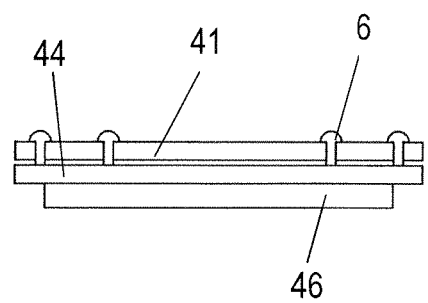

As an alternative to the design shown in FIG. 5a-c, the height of the sensor arrangement can also be reduced. This is shown in FIGS. 6a-6c. In FIG. 6a, the base plate 41 and the electrodes are designed identically to FIG. 5a. In contrast to the electronics board of FIG. 5b, a printed circuit board 44 is provided in FIG. 6b. The contact surfaces can also be formed in an arc shape analogous to FIG. 5b. However, in this variant, the contact surfaces are recessed into the printed circuit board, reducing the overall height of the assembly. An additional carrier plate 46 supports the printed circuit board 44 and provides additional stability.

FIGS. 7a-7c show a variant in which, instead of a uniform base plate, a base plate is arranged rigidly to the substrate and a ring plate 52 is arranged concentrically around the base plate 51. The base plate 51 defines a first inner circular path 56 on which the inner electrodes of a respective electrode assembly 6 and 8 are arranged, while the ring plate 52 has an outer circular path 57 with the outer electrodes of a respective electrode assembly 6 and 8. The ring plate 52 is thereby arranged rotatably relative to the base plate 51. Accordingly, a printed circuit board 53 arranged parallel to the base plate 51 has arc-shaped or ring-segment-shaped contact surfaces 54 for contacting with the outer electrodes on the ring plate 52. A second circular track with arc-shaped contact surfaces for the electrodes of the base plate 51, on the other hand, is not provided and is also not necessary.

The variants of a sensor arrangement shown in FIGS. 8, 9, 10a, and 10b with the depicted alignments of the electrode axes allow virtual rotation of the sensors by changing the electrode assignment of an orthogonal axis alignment. For this purpose, in addition to the two electrode assemblies aligned perpendicularly to one another, at least one further, but preferably two electrode axes, are specified by positioning further electrodes, wherein the electrode axes, starting from one electrode as the angular vertex of both axes, are arranged at an angle, preferably of at least 5 degrees, particularly preferably of at least 10 degrees, to one another. Thus, in addition to the electrode at the angular vertex, at least two of the electrodes of the respective electrode assembly are located on each of the aforementioned axes. The axes are clearly visible in particular from FIGS. 10a and 10b.

The electrodes shown in the preceding figures have primarily a round cross-section. However, it is also possible within the scope of the present invention that other electrode cross-sections, e.g., rectangular electrode cross-sections and/or contact areas, are realized.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

LIST OF REFERENCE SIGNS

1 Measuring device
2 Wristband
3 Display
3.1-3.5 Operating element
4 Measurement transducer
5 Sensor unit
6 Electrode assembly
6.1 Electrode
6.2 Electrode
6.3 Electrode
6.4 Electrode
7 Electrode assembly
8 Electrode assembly
9 Electrode assembly
10 Center point
11 Plate
12 Contact area
13 Line
14 First circular path
15 Second circular path
20 Electrode
21 Inner electrode
22 Electrode shaft
23 Projection
24 Contact surface
25 Signal line
26 Solder connection
27 Support sleeve
28 Channel
29 Projection
31 Base plate
32 Edge
33 Arrow
34 Electronics board
35 Contact surfaces
36 Circular path
37 Circular path
41 Base plate
44 Printed circuit board
46 Carrier plate
51 Base plate
52 Ring plate
53 Printed circuit board
54 Contact surface
56 Inner circular path
57 Outer circular path

The invention claimed is:

1. A measuring device for determining an estimated value for blood sugar content of a person by using a non-invasive impedance measurement, wherein the measuring device comprises:
   a measurement transducer configured to determine the blood sugar content from a measured value; and
   a sensor unit configured to detect the measured value,
   wherein the sensor unit comprises at least two tetrapolar electrode assemblies, each of the at least two tetrapolar electrode assemblies having at least first and second electrode pairs arranged along a respective first linear axis,
   wherein the respective first linear axes of the two tetrapolar electrode assemblies are aligned perpendicularly to one another,
   wherein the first electrode pair of each of the at least two tetrapolar electrode assemblies is configured to emit and receive a current signal, and wherein the second electrode pair of each of the at least two tetrapolar electrode assemblies is configured to tap a potential upon contact with skin of the person,
   wherein each of the electrodes of the electrodes pairs has a contact surface for contacting the skin, wherein the contact surface of each of the electrodes consists of a metal with a conductivity of more than $1*10^7$ S/m or the contact surface of each of the electrodes consists of a metal alloy with a conductivity of more than $1*10^7$ S/m, and
   wherein each of the electrodes comprises an inner electrode consisting of a noble metal and comprises a support sleeve having a channel that is closed off by the inner electrode, wherein the inner electrode extends beyond the support sleeve, wherein the support sleeve is made of
      a material with a Vickers hardness of more than 40 according to DIN EN 6507-1:2018-07, or
      a silicon compound with a Vickers hardness of more than 40 according to DIN EN 6507-1:2018-07, and with a thermal conductivity of more than 100 W/(m*K),
   wherein the sensor unit has a plate or a leather segment on which the at least two tetrapolar electrode assemblies are anchored, wherein the plate or the leather segment has a fatigue bending strength according to DIN EN ISO 5402-1:2017-05 or ISO 4666-2 of 100,000 folds without damage,
   wherein each electrode of the first and second electrode pairs is:
      arranged in an opening of the plate and the support sleeve of each electrode comprises a radial projection on a surface of the plate and at an edge of the opening of the plate as a stop, or
      arranged in an opening of the leather segment and the support sleeve of each electrode comprises a radial projection on a surface of the leather segment and at an edge of the leather segment as a stop.

2. The measuring device of claim 1, wherein the metal is gold, rhodium, tantalum, iridium, or osmium, or the metal alloy is formed by at least 40% by weight of one or more of gold, rhodium, tantalum, iridium, or osmium.

3. The measuring device of claim 1, wherein the noble metal is gold and the support sleeve consists of titanium, steel, alpha silicon carbide, or a beryllium-containing ceramic.

4. The measuring device of claim 1, wherein each of the electrodes comprises an electrode body made of copper, brass, or alpha silicon carbide, wherein the electrode body of each of the electrodes is coated with rhodium, tantalum, iridium, or osmium to form the contact surface of each of the electrodes.

5. The measuring device of claim 4, wherein a thickness of the coating is between 3 to 10 μm.

6. The measuring device of claim 1, wherein a diameter of the contact surface of each electrode is less than 5 mm.

7. The measuring device of claim 1, wherein the each of the electrodes is a mushroom-head electrode having a mushroom-head, wherein the mushroom-head extends beyond the support sleeve of each of the electrodes.

8. The measuring device of claim 1, wherein the at least two tetrapolar electrode assemblies include four or eight tetrapolar electrode assemblies, each of the four or eight tetrapolar electrode assemblies including two electrode pairs arranged on a respective linear axis.

9. The measuring device of claim 1, wherein the electrodes of the first and second electrode pairs are arranged on two circular paths concentrically to one another, wherein a number of electrodes on a first one of the two circular paths is equal to a number of electrodes on a second one of the two circular paths.

10. The measuring device of claim 9, wherein a diameter of the first one of the two circular paths is between 20 to 40 mm and a diameter of the second one of the two circular paths is at least 30% smaller than the diameter of the first one of the two circular paths.

11. The measuring device of claim 9, wherein a distance between two adjacent electrodes of two adjacent electrode assemblies on the first one of the two circular paths is between 5 and 8 mm.

12. The measuring device of claim 1, wherein an arrangement of the electrodes of each of the first and second electrode pairs is mirror-symmetrical.

13. The measuring device of claim 1, wherein the measuring device is a portable measuring device having
a wristband, wherein the sensor unit has a width parallel to the wristband between 15-35 mm, or
an ankle strap, wherein the sensor unit has a width parallel to the ankle strap between 15-35 mm.

14. A measuring device for determining an estimated value for blood sugar content of a person by using a non-invasive impedance measurement, wherein the measuring device comprises:
a measurement transducer configured to determine the blood sugar content from a measured value; and
a sensor unit configured to detect the measured value,
wherein the sensor unit comprises at least two tetrapolar electrode assemblies, each of the at least two tetrapolar electrode assemblies having at least first and second electrode pairs arranged along a respective first linear axis,
wherein the respective first linear axes of the two tetrapolar electrode assemblies are aligned perpendicularly to one another,
wherein the first electrode pair of each of the at least two tetrapolar electrode assemblies is configured to emit and receive a current signal, and wherein the second electrode pair of each of the at least two tetrapolar electrode assemblies is configured to tap a potential upon contact with skin of the person,
wherein each of the electrodes of the electrodes pairs has a contact surface for contacting the skin, wherein the contact surface of each of the electrodes consists of a metal with a conductivity of more than $1*10^7$ S/m or the contact surface of each of the electrodes consists of a metal alloy with a conductivity of more than $1*10^7$ S/m, and
wherein each of the electrodes comprises an inner electrode consisting of a noble metal and comprises a support sleeve having a channel that is closed off by the inner electrode, wherein the inner electrode extends beyond the support sleeve, wherein the support sleeve is made of
a material with a Vickers hardness of more than 40 according to DIN EN 6507-1:2018-07, or
a silicon compound with a Vickers hardness of more than 40 according to DIN EN 6507-1:2018-07, and with a thermal conductivity of more than 100 W/(m*K),
wherein the sensor unit comprises a plate-shaped element, which can be rigidly connected to the person, wherein the at least two tetrapolar electrode assemblies are rotatable relative to the plate-shaped element, and
wherein the plate-shaped element has circular arc-shaped contact surfaces configured to tap signals of electrodes of the at least two tetrapolar electrode assemblies.

15. The measuring device of claim 14, further comprising:
a further electrode assembly having a plurality of further electrodes,
wherein, starting from one of the electrodes of a first one of the two tetrapolar electrode assemblies, the linear axis of the first of the two tetrapolar electrode assemblies is arranged at an angle to a second axis of the further electrode assembly, wherein the signal tapping is controlled by a control unit in such a way that, for a virtual rotation of the first of the two tetrapolar electrode assemblies, the signals are tapped selectively at electrodes of the linear axis of the first one of the two tetrapolar assemblies or plurality of further electrodes of the second axis of the further electrode assembly.

* * * * *